United States Patent
Sato et al.

(10) Patent No.: US 6,667,402 B2
(45) Date of Patent: Dec. 23, 2003

(54) PROCESS FOR PRODUCING ω-MERCAPTOALKYLPYRIDINE

(75) Inventors: Yoshinobu Sato, Toyonaka (JP); Yasuhiro Fukui, Ibaraki (JP); Nobuyasu Fukuda, Hirakata (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/437,075

(22) Filed: May 14, 2003

(65) Prior Publication Data

US 2003/0216578 A1 Nov. 20, 2003

(30) Foreign Application Priority Data

May 16, 2002 (JP) .......................... 2002-141355

(51) Int. Cl.⁷ ............................. C07D 213/32
(52) U.S. Cl. .................................... 546/339
(58) Field of Search ............................... 546/339

(56) References Cited

PUBLICATIONS

Thompson, R.B. et al., Industrial and Engineering Chemistry, vol. 44, No. 7, pp. 1659–1662 (1952).
Chia, P.S.K. et al., Aust. J. Chem., vol. 19, pp. 1835–1845 (1966).
Profft, E. et al., Z. Chem., vol. 1, pp. 19–21 (1961)—(Abstract in English).

Primary Examiner—Patricia L. Morris
(74) Attorney, Agent, or Firm—Birch, Stewart, Kolasch & Birch, LLP

(57) ABSTRACT

The present invention provides a process for producing ω-mercaptoalkylpyridine of the formula (II)

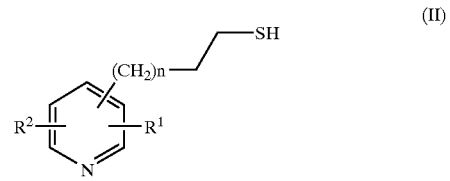

wherein $R^1$ and $R^2$ each independently represent hydrogen or methyl, and n represents an integer of 0 to 2, comprising reacting pyridine compound of the formula (I)

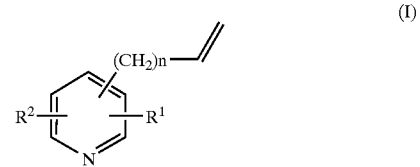

wherein $R^1$, $R^2$ and n have the same meanings described above, and hydrogen sulfide in the presence of tertiary amine.

5 Claims, No Drawings

PROCESS FOR PRODUCING ω-MERCAPTOALKYLPYRIDINE

This nonprovisional application claims priority under 35 U.S.C. §119(a) on patent application Ser. No. 2002-141355 filed in Japan on May 16, 2002, which is herein incorporated by refereence.

FIELD OF THE INVENTION

The present invention relates to a process for producing ω-mercaptoalkylpyridine.

PRIOR ART

ω-Mercaptoalkylpyridine such as 2-(2-mercaptoethyl) pyridine, 4-(2-mercaptoethyl)pyridine and the like are industrially useful compounds as an additive of chelating catalysts for producing bisphenol A; intermediates for medical supplies or agricultural chemicals; and the like.

Conventionally, as the method for producing ω-mercaptoalkylpyridines, there is reported, for example, a method of reacting 2-vinylpyridine with hydrogen sulfide to produce 2-(2-mercaptoethyl)pyridine in a yield of 23% (P. S. K. Chia et al., Aust. J. Chem., 19, 1835 (1966) and R. B. Thompson et al., Industrial and Engineering Chemistry, 44, 1659 (1952)).

An object of the present invention is to provide a process for producing ω-mercaptoalkylpyridines in high yield even if industrially easily available hydrogen sulfide is used.

SUMMARY OF THE INVENTION

The present invention relates to the followings.

<1> A process for producing ω-mercaptoalkylpyridine of the formula (II)

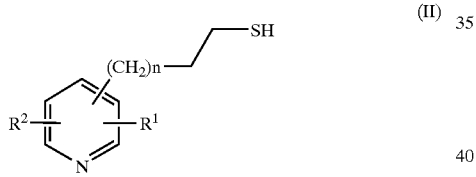

wherein $R^1$ and $R^2$ each independently represent hydrogen or methyl, and n represents an integer of 0 to 2, comprising reacting pyridine compound of the formula (I)

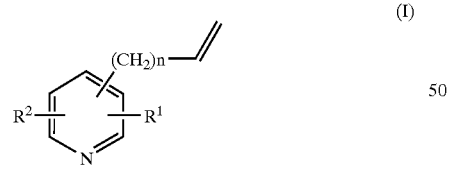

wherein $R^1$, $R^2$ and n have the same meanings described above, and hydrogen sulfide in the presence of tertiary amine, which is hereinafter referred to as "the present process".

<2> The process according to <1> wherein the tertiary amine is at least one tertiary amine compound selected from the group consisting of the following (A) to (C):

wherein $R_{21}$, $R_{22}$ and $R_{23}$ each independently represent alkyl having 1 to 8 carbon atoms, cycloalkyl having 4 to 12 carbon atoms or aromatic hydrocarbon group having 6 to 12 carbon atoms and at least one hydrogen on the alkyl, cycloalkyl or aromatic hydrocarbon group may be substituted by amino, N-alkylamino having 1 to 8 carbon atoms, N,N-diakylamino having 2 to 16 carbon atoms or hydroxy.

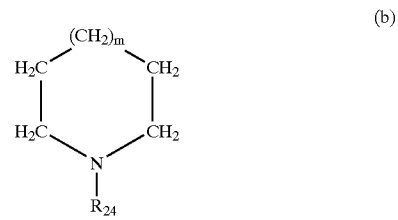

wherein $R_{24}$ represents alkyl having 1 to 8 carbon atoms, cycloalkyl having 4 to 12 carbon atoms or aromatic hydrocarbon group having 6 to 12 carbon atoms, m represents an integer of 0 to 8, and at least one hydrogen atom on —$CH_2$— constituting a ring or on $R_{24}$ may be substituted by amino group, N-alkylamino group having 1 to 8 carbon atoms, N,N-dialkylamino group having 2 to 16 carbon atoms or hydroxyl and one or two —$CH_2$— constituting a ring may be substituted by —NH— or —O—.

(C): Aromatic nitrogen-containing heterocyclic compound wherein at least one hydrogen may be substituted by alkyl having 1 to 8 carbon atoms and at least one hydrogen on the alkyl may be substitutede by amino, N-alkylamino having 1 to 8 carbon atoms or N,N-dialkylamino having 2 to 16 carbon atoms.

<3> The process according to <1> or <2> wherein the pyridine compound of the formula (I) is at least one kind selected from the group consisting of 4-vinylpyridine and 2-vinylpydirine.

<4> The process according to any one of <1> to <3> wherein the tertiary amine is at least one compound selected from the group consisting of tertiary amine of the following formula (1), tertiary amine of the following formula (2), tertiary amine of the following formula (5) and tertiary amine of the following formula (6):

Tertiary amine of the formula (1)

wherein $R^3$ to $R^1$ each independently represent alkyl having 1 to 8 carbon atoms or cycloalkyl having 4 to 12 carbon atoms.

Tertiary amine of the formula (2)

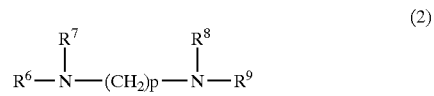

wherein $R^6$ to $R^9$ each independently represent alkyl having 1 to 8 carbon atoms or a cycloalkyl having 4 to 12 carbon atoms, p represents an integer of 1 to 8.

Tertiary amine of the formula (5)

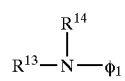

(5)

wherein $R^{13}$ and $R^{14}$ each independently represent alkyl having 1 to 8 carbon atoms or cycloalkyl having 4 to 12 carbon atoms, and $\phi_1$ represents aromatic hydrocarbon group.

Tertiary amine of the formula (6)

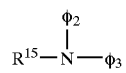

(6)

wherein $R^{15}$ represents alkyl having 1 to 8 carbon atoms or cycloalkyl having 4 to 12 carbon atoms, and $\phi_2$ and $\phi_3$ each independently represent aromatic hydrocarbon group.
<5> The process according to any one of <1> to <4> wherein tertiary amine and pyridine (I) are sequentially mixed with hydrogen sulfide previously filled in a reaction.

DETAILED DESCRIPTION OF PREFERRED EMBODIMENTS

The present invention will be illustrated in detail below.

In the pyridine compound of the formula (I), which is hereinafter referred to as "pyridine (I)", the compound wherein n is 0 is preferable, and pyridine (I) in which both of $R^1$ and $R^2$ represent hydrogen and n is 0 is particularly preferable, and among others, 2-vinylpyridine and 4-vinylpyridine are suitable.

Polymerization inhibitors such as hydroquinones, catechols and the like may be contained usually in an amount of about 0.01 to 0.5% by weight based on pyridine (I), which is sometimes added for deterioration inhibitor of pyridine (I) when stored. It is however recommended that pyridine (I) is purified by simple distillation before the present process.

As hydrogen sulfide used in the present process, that in the form of solution which is dissolved in a solvent such as water, carbon disulfide, methylene chloride and the like may be used, and usually, commercially available compressed hydrogen sulfide contained in a cylinder, gaseous hydrogen sulfide produced, for example, in a factory, and the like, are used as they are. As the specific hydrogen sulfide use method, there are exemplified a method in which hydrogen sulfide is previously introduced into a reaction vessel, then, pyridine (I) and tertiary amine are mixed; a method in which hydrogen sulfide is blown through an introduction tube or the like into a reaction vessel containing mixture of pyridine (I) and tertiary amine; a method in which pyridine (I), tertiary amine and hydrogen sulfide are introduced into a reaction vessel, and the like. For performing the reaction efficiently in use of hydrogen sulfide, the reaction vessel may be sealed, or if necessary, may be pressurized.

The amount of hydrogen sulfide is usually more than 1 mol per 1 mol of pyridine (I), and from the economical standpoint, preferably less than 30 mol. When the reaction is conducted in a sealed vessel, the amount of hydrogen sulfide is usually more than 1 mol per 1 mol of pyridine (I), and from the economical standpoint, preferably less than 10 mol.

The tertiary amine used in the present invention is an amine compound having a nitrogen atom whose three bonds connect with carbon atoms.

Preferred examples of the tertiary amine include at least one organic amine compound selected from the group consisting of the following (A) to (C).

(A): Amine comppund of the formula (a)

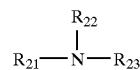

(a)

wherein $R_{21}$, $R_{22}$ and $R_{23}$ each independently represent alkyl having 1 to 8 carbon atoms, cycloalkyl having 4 to 12 carbon atoms or aromatic hydrocarbon group having 6 to 12 carbon atoms and at least one hydrogen on the alkyl, cycloalkyl or aromatic hydrocarbon group may be substituted by amino, N-alkylamino having 1 to 8 carbon atoms, N,N-dialkylamino having 2 to 16 carbon atoms or hydroxy.

(B): Alicyclic amine of the formula (b)

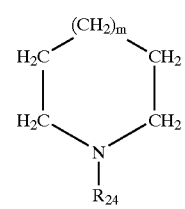

(b)

wherein $R_{24}$ represents alkyl having 1 to 8 carbon atoms, cycloalkyl having 4 to 12 carbon atoms or aromatic hydrocarbon group having 6 to 12 carbon atoms, m represents an integer of 0 to 8, at least one hydrogen atom on —$CH_2$— constituting a ring or on $R_{24}$ may be substituted by amino group, N-alkylamino group having 1 to 8 carbon atoms, N,N-dialkylamino group having 2 to 16 carbon atoms or hydroxyl, and one or two —$CH_2$— constituting a ring may be substituted by —NH— or —O—.

(C): Aromatic nitrogen-containing heterocyclic compound wherein at least one hydrogen may be substituted by alkyl having 1 to 8 carbon atoms and at least one hydrogen on the alkyl may be substitutede by amino, N-alkylamino having 1 to 8 carbon atoms or N,N-dialkylamino having 2 to 16 carbon atoms.

Examples of alkyl group having 1 to 8 carbon atoms in (A), (B) or (C) include methyl, ethyl, butyl and the like. Examples of cycloalkyl having 4 to 12 carbon atoms in (A) include cyclopentyl, cyclohexyl and the like.

Examples of aromatic hydrocarbon group having 6 to 12 carbon atoms in (A) include phenyl, benzyl and the like.

Examples of (A) include tertiary amine having a nitrogen atom bonded to an aromatic hydrocarbon group; weak basic ion exchanged resin having —$CH_2N(CH_3)_2$ on a styrene-divinylbenzene skeleton; and the like.

As the tertiary amines having a nitrogen atom bonded to three alkyl groups, for example, tertiary amines of the following formulae (1) to (4), and the like are listed.

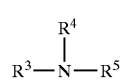

(1)

In the formula (1), $R^3$ to $R^5$ each independently represent alkyl having 1 to 8 carbon atoms or cycloalkyl having 4 to 12 carbon atoms.

Specific examples of the tertiary amine of the formula (1) include trimethylamine, triethylamine, tripropylamine, tributylamine, trioctylamine, diisopropylethylamine, and the like.

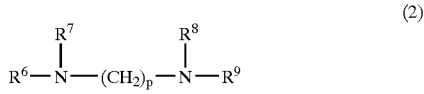

(2)

In the formula (2), $R^6$ to $R^9$ each independently represent alkyl having 1 to 8 carbon atoms or a cycloalkyl having 4 to 12 carbon atoms. p represents an integer of 1 to 8. Specific examples of the tertiary amine of the formula (2) include N,N,N',N'-tetramethyldiaminomethane, N,N,N',N'-tetramethylethylenediamine, N,N,N',N'-tetramethyl-1,3-propanediamine and the like.

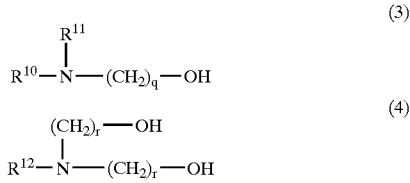

(3)

(4)

In the formulae (3) and (4), $R^{10}$ to $R^{12}$ each independently represent alkyl having 1 to 8 carbon atoms or cycloalkyl having 4 to 12 carbon atoms. q and r each independently represent an integer of 1 to 4.

As the tertiary amine of the formula (3), N,N-diethylethanolamine is exemplified, and as the tertiary amine of the formula (4), N-methyldiethanolamine is exemplified.

As the tertiary amines having a nitrogen atom bonded to an aromatic hydrocarbon group, for example, tertiary amines of the following formulae (5) and (6), and the like are listed.

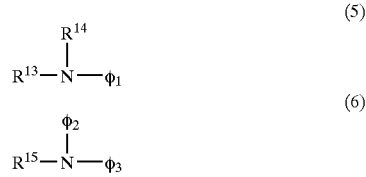

(5)

(6)

Wherein, $R^{13}$ to $R^{15}$ each independently represent alkyl having 1 to 8 carbon atoms or cycloalkyl having 4 to 12 carbon atoms. $\phi_1$ to $\phi_3$ each independently represent aromatic hydrocarbon group.

Specific examples of the tertiary amine of the formula (5) include N,N-dimethylaniline, N,N-diethylaniline and the like. Specific examples of the tertiary amine of the formula (6) include diphenylmethylamine, diphenylethylamine and the like.

Examples of (B) the alicyclic amines of the formula (b) include alicyclic tertiary amines such as bis(aminopropyl) piperazine, N-methylpiperazine, 1-(2-aminoethyl) piperazine, (hydroxyethyl)piperazine, N-methylpiperazine, N-methylmorpholine, N-ethylmorpholine, N-(3-aminopropyl)morpholine, 1,4-diazabicyclo[2,2,2]octane and the like.

Examples of (C) the aromatic nitrogen-containing heterocyclic compounds in which at least one hydrogen atom may be substituted by alkyl group include pyridine, α-picoline, γ-picoline, lutidine, 2-propylpyridine, 4-pyrrolidinopyridine, 4-piperidinopyridine, o-phenanthroline and the like.

As the tertiary amine in the present invention, different two kinds or more of tertiary amines may be used.

As the tertiary amine, preferable are, from the standpoint of the yield of ω-mercaptoalkylpyridine of the formura (II), which is hereinafter referred to as ω-mercaptoalkylpyridine (II), tertiary amines belonging to the above-mentioned (A) and (B), and among them, tertiary amines of the formulae (1), (2), (5) and (6) are more preferable and tertiary amines of the formulae (1) and (2) are particularly preferable.

The amount of the tertiary amine in the present invention may advantageously be 0.005 mol or more per 1 mol of pyridine (I), and the tertiary amine may be used as a solvent.

Specific use amount of the tertiary amine is, in the case of separate use of a solvent, usually from about 0.001 to 1 mol per mol of pyridine (I), and in the case of use as a solvent, usually from about 1 to 100 mol per 1 mol of pyridine (I).

In the present process, a solvent may be used, or production may be effected without using a solvent.

As the solvent, exemplified are organic solvents such as tetrahydrofuran, diethyl ether, methanol, ethanol, isopropanol, acetonitrile, xylene, toluene, benzene, dimethylformamide, acetone, ethyl acetate, hexane, dichloromethane, chloroform and the like.

As the solvent, two kinds or more of solvents may be used.

The present invention is a process for producing ω-mercaptoalkylpyridine (II) comprising reacting pyridine (I) with hydrogen sulfide in the presence of the tertiary amine.

Specifically listed are (i) a method in which hydrogen sulfide is introduced into solution containing the tertiary amine, pyridine (I), and if necessary, solvent; (ii) a method in which hydrogen sulfide is introduced into solution containing the tertiary amine, and if necessary, a solvent, then, pyridine (I) is mixed; (iii) a method in which tertiary amine and pyridine (I) are sequentially mixed with hydrogen sulfide previously filled in a reaction vessel; (iv) a method in which pyridine (I) and tertiary amine are mixed sequentially or in one time with hydrogen sulfide previously filled in a reaction vessel, (v) a method in which the tertiary amine, pyridine (I) and hydrogen sulfide are mixed at one time in a reaction vessel, and the like.

In the process of the present invention, methods of adding pyridine (I) into a reaction vessel previously filled with hydrogen sulfide such as the methods (ii) and (iii) are preferable since production of by-products such as sulfides described later, tends to be suppressed and particularly, the method (iii) is particularly suitable.

The pressure after introduction of hydrogen sulfide (gage pressure, namely, pressure difference based on atmospheric pressure) is from 0.1 to 1.5 MPa, preferably from 0.2 to 1 MPa. The form of hydrogen sulfide in a reaction vessel may be gas or liquid. In pressurizing, inert gas such as nitrogen, helium and the like may be used to control pressure. Further, hydrogen sulfide remaining after completion of the reaction may be transferred to other vessel and re-used in the present process.

The reaction temperature in the present process is usually from about −40 to 100° C., preferably from about −30 to 60° C. When the reaction temperature is −40° C. or higher, the reaction speed tends to increase, and when 100° C. or lower, production of by-products of sulfides such as the compound of the following formula (III) tends to be suppressed.

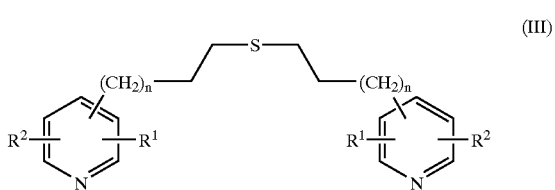

In the formula (III), $R^1$, $R^2$ and n have the same meanings as above.

The reaction time is usually from about 0.1 to 20 hours, though changing depending on the amount ratio of pyridine (I), the tertiary amine and hydrogen sulfide, mixing method, reaction temperature and the like.

The tertiary amine may be removed by concentration under reduced pressure, washing with water, and the like from the resulted reaction mixture to obtain ω-mercaptoalkylpyridine (II). ω-Mercaptoalkylpyridines (II) thus obtained may be used for further reaction without any treatment as a intermediate of, for example, catalyst. Alternatively, the form of ω-mercaptoalkylpyridine (III) may be changed to aqueous solution of the salt thereof by using inorganic acid such as hydrochloric acid, sulfuric acid, nitric acid, phosphoric acid and the like, organic acid such as acetic acid, citric acid and the like.

Further purification can be performed by distilation or by recrystallization of, for example, hydrochloride salt thereof.

The present invention will be illustrated further in detail by experimental examples below, but the scope of the invention is not limited to thereto.

Method of Measuring Yield of 4-(2-Mercaptoethyl) pyridine

The yield of 4-(2-mercaptoethyl)pyridine was measured by diluting solution after the reaction with acetonitrile/water and conducting absolute calibration curve method using liquid chromatography under the following conditions.
<Absolute Calibration Curve Method>
Column: L-column ODS 4.6 mm φ×15 cm
Eluent: acetonitrile/water containing 2.5 mmol/L sodium 1-pentanesulfonate
Detection: UV 254 nm

EXAMPLE 1

Into a vessel was charged 10.5 g (0.1 mol) of 4-vinylpyridine and 0.5 g (0.005 mol) of triethylamine, and 8 g (0.23 mol) of hydrogen sulfide was introduced over 15 minutes while controlling the inner temperature at 10° C. The resulted reaction solution was analyzed by absolute calibration curve method. Yield of 4-(2-mercaptoethyl) pyridine: 71%.

EXAMPLE 2

Into a glass autoclave was introduced 410 g (12.0 mol) of hydrogen sulfide while maintaining positive pressure of 0.5 MPa (gage pressure, 5 kg/cm³), then, mixed solution of 420.8 g (4.0 mol) of 4-vinylpyridine and 37.1 g (0.2 mol) of tributylamine was added by dropping at −10° C. over 7.5 hours while stirring. After completion of adding, the mixture was stirred for 1 hour at −10° C., then, pressure was released to purge remaining hydrogen sulfide. The resulted reaction solution was analyzed by absolute calibration curve method. Yield of 4-(2-mercaptoethyl)pyridine 89%.

EXAMPLE 3

Into an autoclave was introduced 518 g (15.2 mol) of hydrogen sulfide while maintaining positive pressure of 0.8 MPa (gage pressure, 8 kg/cm²), then, mixed solution of 421.6 g (4.0 mol) of 4-vinylpyridine and 23.4 g (0.2 mol) of N,N,N',N'-tetramethylethylenediamine was added by dropping at 5° C. over 3 hours while stirring. After completion of adding, the mixture was stirred for 1 hour at 3° C., then, pressure was released to purge hydrogen sulfide. The resulted reaction solution was analyzed by absolute calibration curve method. Yield of 4-(2-mercaptoethyl)pyridine: 94%.

EXAMPLE 4

The same procedure was repeated as in Example 1 except that triethylamine was substituted by pyridine. The resulted reaction solution was analyzed by absolute calibration curve method. Yield of 4-(2-mercaptoethyl)pyridine: 57%.

COMPARATIVE EXAMPLE 1

The same procedure was repeated as in Example 1 except for not adding triethylamine. The resulted reaction solution was analyzed by absolute calibration curve method. Yield of 4-(2-mercaptoethyl)pyridine: 18%

According to the present invention, ω-mercaptoalkylpyridines can be produced easily and at high yield by the reaction in the presence of tertiary amine in the production of ω-mercaptoalkylpyridines using hydrogen sulfide.

Further, a method of mixing pyridine (I) into a reaction vessel previously filled with hydrogen sulfide can suppress production of by-products such as sulfides and the like, and produce ω-mercaptoalkylpyridines at further excellent yield.

What is claimed is:

1. A process for producing ω-mercaptoalkylpyridine of the formula

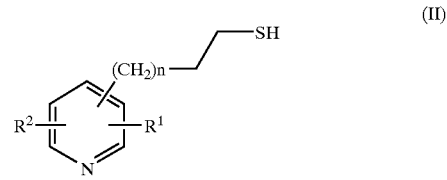

wherein $R^1$ and $R^2$ each independently represent hydrogen or methyl, and n represents an integer of 0 to 2, comprising reacting pyridine compound of the formula (I)

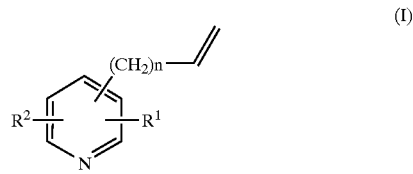

wherein $R^1$ and $R^2$ have the same meanings described above, and hydrogen sulfide in the presence of tertiary amine.

2. The process according to claim 1 wherein the tertiary amine is at least one tertiary amine compound selected from the group consisting of the following (A) to (C);

A: Amine compound of the formula (a)

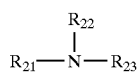
(a)

wherein $R_{21}$, $R_{22}$ and $R_{23}$ each independently represent alkyl having 1 to 8 carbon atoms, cycloalkyl having 4 to 12 carbon atoms or aromatic hydrocarbon group having 6 to 12 carbon atoms and at least one hydrogen on the alkyl, cycloalkyl or aromatic hydrocarbon group may be substituted by amino, N-alkylamino having 1 to 8 carbon atoms, N,N-dialkylamino having 2 to 16 carbon atoms or hydroxy, (B) Alicyclic amine compound of the formula (b)

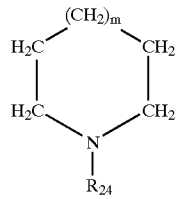
(b)

wherein $R_{24}$ represents alkyl having 1 to 8 carbon atoms, cycloalkyl having 4 to 12 carbon atoms or aromatic hydrocarbon group having 6 to 12 carbon atoms, m represents an integer of 0 to 8, and at least one hydrogen atom on —$CH_2$— constituting a ring or on $R_{24}$ may be substituted by amino group, N-alkylamino group having 1 to 8 carbon atoms, N,N-dialkylamino group having 2 to 16 carbon atoms or hydroxyl and one or two —$CH_2$— constituting a ring may be substituted by —NH— or —O—, (C): Aromatic nitrogen-containing heterocyclic compound wherein at least one hydrogen may be substituted by alkyl having 1 to 8 carbon atoms and at least one hydrogen on the alkyl may be substituted by amino, N-alkylamino having 1 to 8 carbon atoms or N,N-dialkylamino having 2 to 16 carbon atoms.

3. The process according to claim 1 wherein the pyridine compound of the formula (I) is at least one kind selected from the group consisting of 4-vinylpyridine and 2-vinylpydirine.

4. The process according to claim 1 wherein the tertiary amine is at least one compound selected from the group consisting of tertiary amine of the following formula (1), tertiary amine of the following formula (2), tertiary amine of the following formula (5) and tertiary amine of the following formula (6):

Tertiary amine of the formula (1)

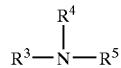
(1)

wherein $R^3$ to $R^5$ each independently represent alkyl having 1 to 8 carbon atoms or cycloalkyl having 4 to 12 carbon atoms, Tertiary amine of the formula (2)

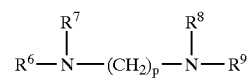
(2)

wherein $R^6$ to $R^9$ each independently represent alkyl having 1 to 8 carbon atoms or a cycloalkyl having 4 to 12 carbon atoms, and p represents an integer of 1 to 8, Tertiary amine of the formula (5)

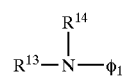
(5)

wherein $R^{13}$ and $R^{14}$ each independently represent alkyl having 1 to 8 carbon atoms or cycloalkyl having 4 to 12 carbon atoms, and $\phi_1$ represents aromatic hydrocarbon group, Tertiary amine of the formula (6)

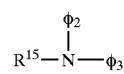
(6)

wherein $R^{15}$ represents alkyl having 1 to 8 carbon atoms or cycloalkyl having 4 to 12 carbon atoms, and $\phi_2$ and $\phi_3$ each independently represent aromatic hydrocarbon group.

5. The process according to claim 1 wherein tertiary amine and pyridine (I) are sequentially mixed with hydrogen sulfide previously filled in a reaction.

* * * * *